United States Patent [19]

Siegemund

[11] Patent Number: 4,992,593

[45] Date of Patent: Feb. 12, 1991

[54] PARTIALLY FLUORINATED DIPHENYL ETHERS, PROCESSES FOR THEIR PREPARATION AND THEIR USE

[75] Inventor: Günter Siegemund, Hofheim am Taunus, Fed. Rep. of Germany

[73] Assignee: Hoechst Aktiengesellschaft, Frankfurt am Main, Fed. Rep. of Germany

[21] Appl. No.: 275,787

[22] Filed: Nov. 23, 1988

[30] Foreign Application Priority Data

Nov. 24, 1987 [DE] Fed. Rep. of Germany ....... 3739795

[51] Int. Cl.⁵ .............................................. C07C 41/00
[52] U.S. Cl. .................................... 568/637; 568/639
[58] Field of Search ...................... 568/637, 641, 639

[56] References Cited

U.S. PATENT DOCUMENTS

| | | | |
|---|---|---|---|
| 3,310,573 | 3/1967 | Coe | 260/346.3 |
| 3,355,500 | 11/1967 | Farah et al. | 260/613 |
| 3,449,296 | 6/1969 | Angelo et al. | 260/47 |

FOREIGN PATENT DOCUMENTS 0192480 8/1986 European Pat. Off. .

OTHER PUBLICATIONS

Gibbs et al, *ACS Polym. Prep.*, vol. 15, No. 1, pp. 775-780 (1974).
Hitachi, Chemical Abstracts, vol. 100, No. 139807v (1984).

*Primary Examiner*—Bruce Gray

[57] ABSTRACT

A compound of the formula

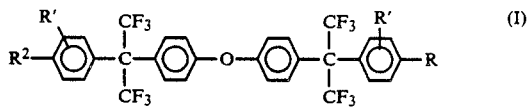

in which independently of one another R is equal to OH or lower alkyl having 1 to 4 carbon atoms, R' is equal to hydrogen or lower alkyl having 1 to 4 carbon atoms, processes for their preparation and their use as starting material in the preparation of partially fluorinated polycondensates.

6 Claims, No Drawings

PARTIALLY FLUORINATED DIPHENYL ETHERS, PROCESSES FOR THEIR PREPARATION AND THEIR USE

DESCRIPTION

Partially fluorinated diphenyl ethers, processes for their preparation and their use.

The invention relates to novel, partially fluorinated diphenyl ethers, to processes for their preparation in the presence of hydrogen fluoride and their use as intermediates for building blocks of partially fluorinated polycondensates.

Partially fluorinated diphenyl ethers are known. Thus, U.S. Pat. No. 3,355,500 describes the preparation of 4,4'-bis(hexafluoro-2-hydroxy-2-propyl)diphenyl ethers. Diarylfluoro compounds in which two substituted phenylene rings are connected via a hexafluoroisopropylidene bridge are known from U.S. Pat. No. 3,310,573 are from I. L. Knunyants et al., Izv. Akad. Nauk. SSSR, Otdel. Khim. Nauk. 4. 666–692 (1960), English edition p. 647–653 (1960). The reaction of the known dihydroxy compounds in the presence of hydrogen fluoride to give higher-molecular-weight products which are connected via two hexafluoroisopropylidene bridges can, however, not be found in the prior art.

The invention relates to compounds of the formula

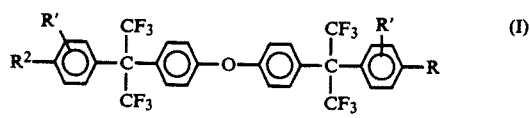

in which independently of one another R is equal to OH or lower alkyl having 1 to 4 carbon atoms and R' is equal to hydrogen or lower alkyl having 1 to 4 carbon atoms, alkyl being preferably $CH_3$, and to a process for their preparation and their use. In formula I, the radical R' is preferably in the o-position with respect to the radical R.

The compounds according to the invention can in general be prepared by two processes, specifically (a) by condensation of one mol of a dicarbinol ($a_1$) of the formula

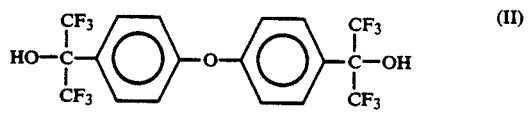

with at least 2 mol of an aromatic substituted hydrocarbon ($a_2$) of the formula

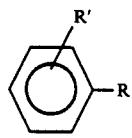

or (b) by condensation of at least 2 mol of a compound ($b_1$) of the formula

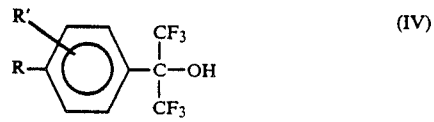

with one mol of diphenyl ether (V) ($b_2$) in the presence of hydrogen fluoride. Examples of aromatic substituted hydrocarbons (III) are phenylene compounds which are substituted by OH and/or alkyl radicals having 1 to 4 carbon atoms such as phenol, toluene, the various xylenes and cresols. Compounds of the formula (II) which can be used in process (a) are described in U.S. Pat. No. 3,355,500.

Compounds of the formula (IV) which can be converted to the compounds according to the invention according to process (b) are also known and described in J. O. C. 30 p. 998–1001 (1965). These compounds are reacted with diphenyl ether.

The reaction temperatures in processes (a) and (b) are between 80° and 180° C., preferably between 100° and 170° C.

The reaction times are in general 24 to 90, preferably 65 to 90, hours.

The molar ratio of the reactants used is determined in process (a) by the ratio of compounds (II): compounds (III), and in process (b) by the ratio of diphenyl ether: compounds (IV), and is in both cases in general at least 1:2, preferably 1: (2.2 to 4).

The amount of hydrogen fluoride (HF), which is necessary in the reaction for the preparation of the compounds according to the invention, is based in process (a) on compound (II) and is in general present in a molar ratio of 1: (7 to 25), preferably 1: (10 to 20). In process (b), the molar ratio of compounds (IV): (HF) is in general 1: (6 to 15), preferably 1: (8 to 13).

The reaction product is in general worked up by blowing out the hydrogen fluoride from the reactor at about 80° C., after the reaction is completed, and removing the remaining residue, with or without dilution with an organic solvent, for example at room temperature, from the reactor. The crude mixture obtained is mixed with water, washed and separated off. The reaction product can be further purified by subjecting it to recrystallization from an organic solvent with or without pretreatment with activated carbon, or by stirring it up in organic solvents, preferably in chloropropane or methanol. Suitable solvents which can be used for the work up are aliphatic hydrocarbons having 5 to 10 carbon atoms, aliphatic monoalcohols having 1 to 4 carbon atoms in the alkyl radical and monochlorinated or polychlorinated aliphatic hydrocarbons having 1 to 4 carbon atoms in the alkyl radical. Examples of these are n-hexane, n-heptane, methanol, ethanol, the various propanols and butanols, and cholorpropane and di- and tri-chloromethane. In general, the purified products are obtained as colorless crystals.

Special novel, partially fluorinated diphenyl ethers in the context of the invention are:
4,4'-bis[2-(4-hydroxyphenul)hexafluoroisopropyl]diphenyl ether, 4,4'-bis[2-(4-methylphenyl)hexafluoroisopropyl]diphenyl ether, 4,4'-bis[2-(3,4-dimethylphenyl)hexafluoroisopropyl]diphenyl ether.

The novel compounds can be used for the preparation from which synthetic building blocks of partially fluorinated polycondensates can be produced, for example polyesters, polyamides and polyimides, such as have been described in the Patent Applications of the same day U.S. Ser. No. 275,405 (HOE 87/F 351 K) "Partially fluorinated carboxylic acids and derivatives thereof, processes for this preparation and use" and U.S. Ser. No. 276,194 (HOE 87/F 353 K) "Fluoro-containing compounds based on 4,4'-bis[2-(4-hydroxyphenyl)hexafluoroisopropyl]diphenyl ether, processes for their preparation and their use".

Allowed U.S. patent application Ser. No. 07/275,405, states at page 3, lines 21-26 that "[t]he partly fluorinated tetracarboxylic acids and their dianhydrides are thus, for example, units for polyimides which can be used for industrially important purposes, for example for coatings and adhesives exposed to high degrees of heat in aircraft construction or in microelectronics". Allowed U.S. patent application Ser. No. 07/276,194, states at page 5, lines 15-18 that "[t]he 4,4'-bis[2-(3-amino-4-hydroxyphenyl)hexafluoroisopropyl]diphenylether according to the invention can also serve as monomer for such polyamides and polybenzoxazoles". As set forth in the allowed copending U.S. Application Ser. No. 07/275,405 filed Nov. 23, 1988, diphenyl ethers 4,4'-bis[2-(4-methylphenyl)hexafluoroisopropyl]diphenylether and 4,4'-bis[2-(3,4-dimethylphenyl)hexafluoroisopropyl]diphenyl ether are used to prepare di- and tetracarboxylic acids with a 12F radical. And as set forth in allowed copending U.S. Application Ser. No. 07/276,194 filed Nov. 23, 1988, the starting material for the novel compound defined by the following structural formula I

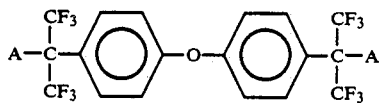

in which A represents the radicals

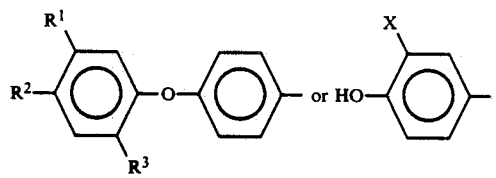

in which $R^1$ and $R^2$ are different from one another and denote hydrogen, $-NO_2$ or $-NH_2$, $R^3$ is hydrogen or halogen, X represents $-NO_2$ or $NH_2$, with the proviso that $R^1$ is hydrogen, if $R^2$ is $-NO_2$ or $-NH_2$ and $R^2$ is hydrogen, if $R^1$ is $-NO_2$ or $-NH_2$ is the 4,4'-bis[2-(4-hydroxyphenyl)hexafluoroisopropyl]diphenyl ether.

In the examples which follow stainless steel means chromium-nickel steel.

EXAMPLES (1) 4,4'-Bis[2-(4-hydroxyphenyl)hexafluoroisopropyl]diphenyl ether (a) In a 1 L stirred autoclave made of stainless steel, 251 g of 4,4'-bis[hexafluoro-2-hydroxy-2-propyl]diphenyl ether, 94 g of phenol and 180 g of anhydrous hydrogen fluoride were combined and stirred for 72 hours at 120° C. After the hydrogen fluoride had been blown out, the partially solid product was suspended in etha-nol and removed from the autoclave. The crude product was dissolved by heating in the presence of 30 g of activated carbon, from which solution, after cooling, 278 g of crystalline product, namely 4,4'-bis[2-(4-hydroxyphenyl)hexafluoroisopropyl]diphenyl ether (yield: 85%) precipitated, which, after washing with water and drying, had a melting point of 179° to 180° C.

Analysis for $C_{30}H_{18}F_{12}O_3$:
calculated: C 55.04% H 2.75% F 34.86%
found: C 55.00% H 2.60% F 35.10%

(b) A 2 L stainless steel reactor was filled with 68 g of 4,4'-bis[hexafluoro-2-hydroxy-2-propyl]diphenyl ether, 282 g of phenol and 450 g of anhydrous hydrogen fluoride. The condensation reaction was carried out at 140° C. for 66 hours with stirring. After the temperature had been lowered to 80° C., the hydrogen fluoride was blown out. The solid product was then removed from the autoclave, thoroughly washed with water and dried with $CaCl_2$. The product was purified by suspending it in 1.5 L of chloropropane and stirring it for several hours. After the solvent had been separated off and the product had been dried, 717 g of crystalline product (yield: 81.2%) were obtained, which, according to the gas chromatogram, was 99/1% pure. Melting point: 179° to 180° C.

(c) In a 1 L stainless steel autoclave equipped with stirrer, 286 g of 2-(4-hydroxyphenyl)hexafluoro-2-propanol and 85 g of diphenyl ether were initially introduced. 200 g of anhydrous hydrogen fluoride were then pumped into the sealed autoclave. The reaction was carried out at 120° C. for 65 hours. The hydrogen fluoride was then blown out at 80° C. the solid residue suspended in water and flushed out of the autoclave. After washing the product with water, activated carbon and ethanol were added, the mixture was heated for 2 hours, filtered and the filtrate was cooled. Yield 154 g = 47%. Melting point: 179° to 180° C.

(2) 4,4'-Bis[2-(4-methylphenyl)hexafluoroisopropyl]diphenyl ether.

(a) 825 g of 2-(4-methylphenyl)hexafluoro-2-propanol, 256 g of diphenyl ether and 540 g of anhydrous hydrogen fluoride were heated in a 2 L stainless steel autoclave for 65 hours at 170° C. with stirring. At 80° C., the hydrogen fluoride was subsequently blown out; 500 ml of n-hexane were added to the cooled residue, the mixture was stirred up and removed from the autoclave by suction. The organic phase was washed twice with water, the n-hexane was distilled off, and the residue (775 g) was stirred together with 1.5 l of methanol. The solid product (587 g or 60.2% yield) was separated off from the methanol and dried. Melting point: 89 to 90.5° C.

Analysis for $C_{32}H_{22}F_{12}O$:
calculated: C 59.08% H 3.38% F 35.08%
found: C 59.50% H 3.35% F 35.10%

(b) In a 1 l steel autoclave equipped with stirrer, 387 g of 2-(4-methylphenyl)hexafluoro-2-propanol, 128 g of diphenyl ether and 270 g of anhydrous hydrogen fluoride were combined and stirred for 64 hours at 150° C. At 80° C., the hydrogen fluoride was subsequently blown out, the product removed from the autoclave by suction and diluted with 200 ml of methylene chloride. The organic solution was washed twice with water, dried over $CaCl_2$ and concentrated by distillation. 401 g remained, which were dissolved in 400 ml of n-hexane, filtered off with suction through a sintered glass crucible using a filtration aid and separated from the solvent by distillation. The residue (385 g or 79% yield) was recrystallized from 400 ml of ethanol. Melting point: 89° to 90° C.

(3) 4,4′-Bis[2-(3,4-dimethylphenyl)hexafluoroisopropyl]diphenyl ether.

(a) 256 g of diphenyl ether and 812 g of 2-(3,4-dimethylphenyl)-hexafluoro-2-propanol were initially introduced into a 2 l stainless steel autoclave, and 540 g of anhydrous hydrogen fluoride were then pumped in. The reaction mixture was subsequently maintained at 150° C. for 65 hours with stirring. After the hydrogen fluoride had been evaporated at 80° C., the product was cooled to room temperature, 250 ml of n-hexane were added and the mixture was removed from the autoclave. After heating to reflux for a short time, 466 g of product crystallized from the n-hexane solution upon cooling, which, after recrystallization from ethanol, had a melting point of 140° to 141° C. Yield: 45.8%.

Analysis for $C_{34}H_{26}F_{12}O$:
calculated: C 60.18% H 3.83% F 33.63%
found: C 60.15% H 3.80% F 33.70%

(b) 312 g of 4,4′-bis(hexafluoro-2-hydroxy-2-propyl)-diphenyl ether and 268 g of o-xylene were placed in a 2 l stainless steel autoclave, and 300 g of anydrous hydrogen fluoride were subsequently pumped into the sealed autoclave. The reaction mixture was stirred at 120° C. for 87 hours. After the hydrogen fluoride had been blown out at 80° C., the product cooled to room temperature was removed from the autoclave and poured into ice water. The organic phase was diluted with 200 ml of dichloromethane, and the solution was dried over $CaCl_2$. After methylene chloride and excess o-xylene had been distilled off, 358 g of residue remained, which, after treatment with 35 g of activated carbon and recrystallization from 400 ml of chloroform, had a melting point of 139° to 141° C. Yield: 85.2%.

I claim:
1. A compound of the formula

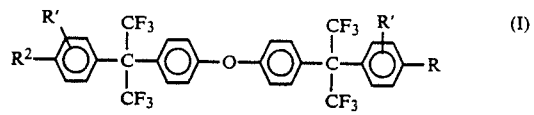

in which independently of one another R is equal to OH or lower alkyl having 1 to 4 carbon atoms, R′ is equal to hydrogen or lower alkyl having 1 to 4 carbon atoms.

2. A compound as claimed in claim 1, wherein lower alkyl is the —$CH_3$ group.

3. A compound as claimed in claim 1, wherein R′ is in the ortho-position with respect to the radical R.

4. 4,4′-Bis[2-(4-hydroxyphenyl)hexafluoroisopropyl]-diphenyl ether.

5. 4,4′-Bis[2-(4-methylphenyl)hexafluorisopropyl]-diphenyl ether.

6. 4,4′-Bis[2-(3,4-dimethylphenyl(hexafluorisoproply]diphenyl ether.

* * * * *

UNITED STATES PATENT AND TRADEMARK OFFICE
CERTIFICATE OF CORRECTION

PATENT NO. : 4,992,593
DATED : February 12, 1991
INVENTOR(S) : Gunter Siegemund It is certified that error appears in the above-identified patent and that said Letters Patent is hereby corrected as shown below:

At col. 1, line 24, "666-692" should read --668-692--.

At col. 1, line 35 Formula (I) should read:

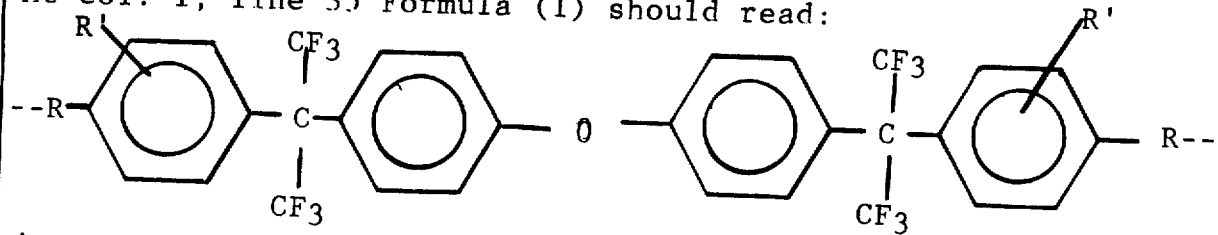

At col. 2, line 65 "(4-hydroxyphenul)" should read --(4-hydroxyphenyl)--.

At col. 3, line 2 "from which" should read --of--.

At col. 3, line 2 "of" should read --from which--.

At col. 3, line 8 "this" should read --their--.

At col. 4, line 25 "99/1%" should read --99.1%--.

In claim 1 (col. 6, line 12) Formula (I) should read:

UNITED STATES PATENT AND TRADEMARK OFFICE
CERTIFICATE OF CORRECTION

PATENT NO. : 4,992,593    page 2 of 2

DATED : February 12, 1991

INVENTOR(S) : Gunter Siegemund

It is certified that error appears in the above-identified patent and that said Letters Patent is hereby corrected as shown below:

In claim 1 (col. 6, line 12) Formula (I) should read:

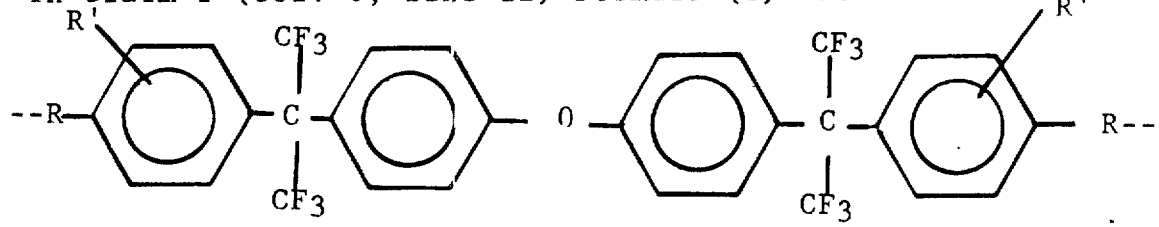

In claim 6 (col. 6, line 29) "ply]diphenyl" should read --pyl]diphenyl--.

Signed and Sealed this

Twenty-second Day of September, 1992

Attest:

DOUGLAS B. COMER

Attesting Officer    Acting Commissioner of Patents and Trademarks